United States Patent
Morfill et al.

(10) Patent No.: US 11,628,050 B2
(45) Date of Patent: Apr. 18, 2023

(54) DEVICE AND METHOD FOR TREATING OBJECTS, IN PARTICULAR DENTAL PROSTHETICS AND/OR TEETH

(71) Applicant: terraplasma GmbH, Garching (DE)

(72) Inventors: Gregor Morfill, Munich (DE); Julia Zimmermann, Munich (DE); Tetsuji Shimizu, Tsukuba Ibaraki (JP); Yangfang Li, Olching (DE); Sylvia Binder, Ebersberg (DE); Maximilian Cantzler, Ebersberg (DE); Hannes Weilemann, Munich (DE)

(73) Assignee: Terraplasma GmbH, Garching (DE)

( * ) Notice: Subject to any disclaimer, the term of this patent is extended or adjusted under 35 U.S.C. 154(b) by 490 days.

(21) Appl. No.: 16/075,176

(22) PCT Filed: Feb. 3, 2017

(86) PCT No.: PCT/EP2017/052425
§ 371 (c)(1),
(2) Date: Nov. 2, 2018

(87) PCT Pub. No.: WO2017/134243
PCT Pub. Date: Aug. 10, 2017

(65) Prior Publication Data
US 2019/0076225 A1    Mar. 14, 2019

(30) Foreign Application Priority Data
Feb. 5, 2016    (DE) .................... 10 2016 201 818.3

(51) Int. Cl.
*A61C 17/00* (2006.01)
*A61N 1/44* (2006.01)
(Continued)

(52) U.S. Cl.
CPC ............ *A61C 17/036* (2013.01); *A61C 17/02* (2013.01); *A61C 19/063* (2013.01); *A61L 2/14* (2013.01);
(Continued)

(58) Field of Classification Search
CPC ..... A61C 17/036; A61C 17/02; A61C 19/063; A61L 2/14; A61L 2/18; A61L 2/183;
(Continued)

(56) References Cited

U.S. PATENT DOCUMENTS 8,277,616 B2    10/2012    Liu et al.
2011/0076190 A1*    3/2011    Tanaka ..................... C02F 1/72
                                                                    422/28
(Continued)

FOREIGN PATENT DOCUMENTS

DE    10 2006 015 694    10/2007
EP    3067007    9/2016
(Continued)

OTHER PUBLICATIONS

International Search Report and Written Opinion for corresponding Patent Application No. PCT/EP2017/052425 dated Mar. 31, 2017.

*Primary Examiner* — Xiuyu Tai
(74) *Attorney, Agent, or Firm* — Renner, Otto, Boisselle & Sklar, LLP

(57) ABSTRACT

The invention relates to a device (1) for treating objects, in particular dental prosthetics and/or teeth, comprising a receiving volume (3) for receiving a cleaning fluid (5), a plasma source (7) configured to generate a non-thermal plasma (35), wherein the device (1) is configured for mixing a plasma product with the cleaning fluid (5), whereby an activated cleaning fluid can be generated, and wherein the
(Continued)

device (1) is configured for using the activated cleaning fluid on an object, in particular on at least one dental prosthesis and/or at least one tooth.

15 Claims, 5 Drawing Sheets

(51) Int. Cl.
  *A61C 17/02* (2006.01)
  *A61C 19/06* (2006.01)
  *A61L 2/14* (2006.01)
  *A61L 2/18* (2006.01)
(52) U.S. Cl.
  CPC ............... *A61L 2/18* (2013.01); *A61L 2/183* (2013.01); *A61L 2/186* (2013.01); *A61N 1/44* (2013.01); *A61L 2202/11* (2013.01); *A61L 2202/122* (2013.01); *A61L 2202/21* (2013.01)
(58) Field of Classification Search
  CPC ............ A61L 2/186; A61L 2202/11; A61L 2202/122; A61L 2202/21; A61L 9/145; A61L 2/208; A61L 2/22; A61L 9/14; A61L 9/22; A61L 2202/15; A61L 2202/25; A61L 2209/134; A61L 2209/213; A61N 1/44; F24D 17/0073; F24D 17/0078; F24D 17/02; C02F 1/4672; C02F 1/72; C02F 1/4608; C02F 1/78; C02F 1/32; C02F 2303/04; C02F 2201/46105; C02F 2201/46175; C02F 2209/005; C02F 2209/10; C02F 2103/008; C02F 2209/02; C02F 2209/05; C02F 2209/06; C02F 2209/11; C02F 2209/22; H05H 1/36; H05H 1/2406; H05H 2240/20; H05H 2245/125; H05H 2245/1225; H05H 2245/123; H05H 2001/2412; H05H 1/24; H05H 1/48; H05H 2245/121; B05B 7/249; B05B 17/04

See application file for complete search history.

(56) References Cited

U.S. PATENT DOCUMENTS

| 2013/0272929 | A1  |  10/2013 | Pelfrey et al. |
| 2015/0004559 | A1* |  1/2015  | Luettgen ............... A61C 1/0092 |
|              |     |          |                              433/80 |
| 2015/0239759 | A1* |  8/2015  | Kang ........................ C02F 1/78 |
|              |     |          |                           210/748.17 |
| 2016/0244683 | A1* |  8/2016  | Gomaa ................ H05H 1/2406 |
| 2018/0133496 | A1* |  5/2018  | Zuidervaart ............. A61N 1/44 |

FOREIGN PATENT DOCUMENTS

| JP | 2008-302198 |   | 12/2008 |
| KR | 10-0918474  |   | 9/2009  |
| WO | WO 2009/128579 | * | 10/2009 |
| WO | 2010/103263 |   | 9/2010  |
| WO | 2011/123124 |   | 10/2011 |
| WO | 2015/083155 |   | 6/2015  |

* cited by examiner

DEVICE AND METHOD FOR TREATING OBJECTS, IN PARTICULAR DENTAL PROSTHETICS AND/OR TEETH

The invention relates to a device as well as a method for treating, in particular cleaning, objects, in particular dental prosthetics and/or teeth.

BACKGROUND

For cleaning dental prosthetics, in particular outside of the mouth, typically chemical solutions are used that for example are provided by means of effervescent tablets that dissolve in water. In this case, comparatively high concentrations of cleaning chemicals are used, and the cleaning solutions are typically unsuitable for consumption; dental prosthetics cleaned in this manner therefore must be thoroughly rinsed after being cleaned before they can be reinserted into the mouth. Typically chemicals are also used to clean teeth, in particular in the form of toothpaste, that should not be swallowed. Typically concentrations of hydrogen peroxide are used to whiten dental prosthetics and/or teeth that lie far above the threshold value applicable in the European Union for nonprofessional tooth whiteners or drinking water. Corresponding preparations therefore cannot be used, or can only be used by trained personnel, directly in the mouth, and the same problem results with regard to the drinkability of a whitening solution for dental prosthetics that was described above with respect to cleaning solutions. In addition, the above-described cleaning and/or whitening solutions are involved to produce, wherein chemicals that must be additionally procured always have to be accessed.

SUMMARY OF THE INVENTION

The object of the invention is to create a device and method for treating, in particular cleaning, objects, in particular dental prosthetics and/or teeth, wherein the aforementioned disadvantages do not occur.

The object is achieved by creating the objects of the independent claims. Advantageous embodiments will become apparent from the dependent claims.

The object is in particular achieved in that a device for treating, in particular cleaning, objects, in particular dental prosthetics and/or teeth is created that has a receiving volume for receiving a cleaning fluid, wherein the device moreover has a plasma source that is configured to generate a non-thermal plasma. The device is configured to mix a plasma product of the nonthermal plasma with the cleaning fluid, whereby an activated cleaning fluid can be generated. Moreover, the device is configured to use the activated cleaning fluid on an object, in particular on at least one dental prosthetic and/or at least one tooth.

Wherever dental prosthetics and/or teeth are referenced here and in the following, these specific exemplary embodiments are always addressed as well as analogously other objects for which the activated cleaning fluid can be correspondingly used.

By means of the plasma source, a nonthermal plasma can be provided without accessing additionally procured chemicals, wherein in particular additional chemicals do not need to be accessed when water is used as the cleaning fluid. The activated cleaning fluid that ultimately serves as an agent for treating dental prosthetics and/or teeth can therefore be provided easily, straightforwardly, quickly and economically. It was also revealed that a cleaning fluid that on one hand is highly effective and on the other hand is compatible with drinking water standards can be provided by means of plasma activation of a cleaning fluid, in particular water, which can be readily also used directly in the mouth and can be swallowed, wherein in addition a dental prosthetic that is cleaned outside of the mouth does not have to be thoroughly rinsed in the same way as with conventional chemical cleaning solutions since the activated cleaning fluid can have the quality of drinking water.

"Treatment of objects", in particular dental prosthetics and/or teeth, is understood in this case to mean in particular cleaning, more particularly disinfecting and in particular reducing a bioburden on objects, in particular dental prosthetics and/or teeth, by bacteria and/or viruses, as well as in addition or alternatively whitening dental prosthetics and/or teeth. In particular, the treatment is preferably not a medical treatment, but rather a treatment to be performed in the context of daily dental or dental prosthetic hygiene, also in particular prophylactic or cosmetic treatment.

The invention relates in particular to a device as well as a method for hygienically and/or cosmetically treating objects, in particular dental prosthetics and/or teeth.

A "receiving volume" is in particular understood to be a spatial region in the device that is suitable for receiving a cleaning fluid. In this case, "receive" is understood to be both statically holding as well as conducting the cleaning fluid through the receiving volume. Preferably, the receiving volume is designed as a closed volume or provided such that it can be closed by a covering apparatus so that a closed volume can be provided by means of the covering apparatus.

A "cleaning fluid" is understood in particular to be a fluid medium that can serve as the carrier substance, in particular as a solvent, for active species in the nonthermal plasma and/or the plasma product, and accordingly can be used to clean in particular dental prosthetics and/or teeth. Particularly preferably, a medium is used as the cleaning fluid that is liquid under normal conditions, i.e., at 25° C. and 1013 mbar. A particularly preferred cleaning fluid is water.

A "nonthermal plasma" is in particular understood to be a plasma in which a temperature describing the distribution of kinetic energy of the plasma electrons which is also termed the electron temperature, is not identical with, and in particular very much higher than a temperature describing the distribution of kinetic energy of the ions comprised by the plasma, in particular atom ions or molecular ions, which is also termed the ion temperature. In this case, the electron temperature is very much higher than the ion temperature, wherein the ion temperature can in particular be chosen within a range of 25° C. to at most 100° C. Such a plasma is also termed a cold plasma due to the comparatively low ion temperature.

Particularly preferably, the plasma source is configured to generate such a nonthermal or cold plasma at atmospheric pressure, in particular at approximately 1013 mbar, wherein such a plasma is also termed an atmospheric plasma.

In this case, a plasma in particular designates a material state in which charged particles are next to each other with different charges in the gas phase, wherein averaged over a specific volume, a neutral electrical charge for the relevant volume results. The plasma moreover preferably comprises uncharged atoms and/or molecules that are in electronically, vibrationally or rotationally excited states, and that are also termed excited particles, and/or free radicals, and overall are therefore termed in particular reactive atoms and/or molecules that are also termed reactive particles or reactive species.

A "plasma product" is in particular understood to be the nonthermal plasma itself, or at least one component or product of the nonthermal plasma, wherein the plasma product in particular has active and/or reactive species that are a component of the nonthermal plasma, or originate from the nonthermal plasma. The plasma product therefore does not necessarily comprise the above-defined material state in which particles with different charges are next to each other. It is in particular possible for the actual plasma to have already ceased in a narrow sense while the plasma product still exists. The plasma product preferably has in particular ionized components, and/or excited or activated neutral components.

Here and in the following, "plasma-containing air" or plasma-containing gas" is understood in particular to be air or gas that has the plasma product, i.e., in particular active and/or reactive species, that are a component of the generated plasma or originate from the generated plasma. It is not absolutely necessary for the air or gas to actually have a plasma in the narrower sense of the above-defined material state. Instead, for the property of "plasma-containing", it is preferably enough for the air or gas to comprise still active and/or reactive species that were generated in the plasma or together with the plasma.

A "plasma source" is in particular understood to be an apparatus that is designed to generate a nonthermal plasma, in particular an atmospheric plasma. Preferably, it is an electrical and/or electronic apparatus, wherein the plasma is generated by an electric discharge, in particular a dielectric barrier discharge, a corona discharge, or another form of discharging suitable for generating a nonthermal plasma. Particularly preferably, the plasma source is formed as a surface microdischarge (SMD) as for example describe in the international patent application with publication number WO 2010/094304 A1, or according to the self-sterilizing surface (SSS) principle as for example described in European patent applications EP 2 387 907 A1, WO 2011/144344 A2 and WO 2011/110343 A1. It is also possible for the plasma source to be formed according to the dielectric barrier discharge (DBD) principle. The cited applications and documents are included here by way of reference with regard to the design of the plasma source. It is in particular possible for the plasma source to have a first electrode and a second electrode, wherein the first electrode is at a distance from the second electrode by at least one dielectric. In this case, at least one of the electrodes can be arranged on a surface of the dielectric, and/or embedded in the surface of the dialectic. In this way, it is possible to generate a plasma directly on a surface of the dielectric. The plasma source can have a flat, in particular planar electrode arrangement, in particular when it is integrated in a covering apparatus. It is however also possible for the plasma source to have a curved, in particular cylindrical, or a round, oval or polygonal shape that generally encloses an interior, in particular when it is arranged in a medium line for conducting a gaseous medium. It is however also possible to arrange at least one planar plasma source or plurality of planar plasma sources in such a medium line, in particular in the form of a stacked arrangement. A perforated electrode arrangement through which a gaseous medium can flow is also possible.

The electrode arrangement of the plasma source including the dielectric can be designed very thin. In particular, it can have a thickness of 20 μm up to a few 100 μm, in particular 20 μm to at most 500 μm, preferably up to at most 300 μm. Such a thin electrode arrangement is flexible and can easily be brought into a shape that is desirable and in particular useful for the device.

A "mixture of the plasma product with the cleaning fluid" is in particular understood to mean that the plasma and/or in particular the reactive species comprised by the plasma or originating from the plasma are brought into contact with the cleaning fluid such that they react therewith and/or are absorbed by the cleaning fluid. The mixture can for example be achieved by shaking, atomizing the cleaning fluid in a region in which the plasma product is arranged, and/or by aerating the cleaning fluid with plasma-containing gas, in particular plasma-containing air, in particular by supplying plasma-containing gas or air into the cleaning fluid.

An "activated cleaning fluid" is in particular understood to be the cleaning fluid after being mixed with the plasma product, wherein the cleaning fluid has species from the plasma, reaction products with the plasma product, and/or solvatized species or reaction products of the plasma product. In particular, such species lend the cleaning fluid its cleaning, in particular disinfecting and/or whitening effect.

Using the activated cleaning fluid on at least one object, in particular on at least one dental prosthetic and/or at least one tooth, is in particular understood to mean an application of the activated cleaning fluid for the purpose of cleaning, in particular disinfecting, and/or for whitening the at least one object, in particular at least one dental prosthetic and/or at least one tooth. The application can in this case be in particular in the mouth or however also outside of the mouth, for example in the receiving volume itself.

According to a development of the invention, the plasma source is arranged to act on an air space arranged above a fill level of the cleaning fluid in the receiving volume. In this case, an air space is arranged in the device above a fill level of the cleaning fluid for which for example a fill level mark can be provided, wherein the plasma source is arranged relative to the receiving volume and the relevant air space so that a plasma can be generated by means of the plasma source in the air space. The plasma is therefore preferably not generated directly in the cleaning fluid, but rather in the airspace above the cleaning fluid. It is in particular possible for the plasma source to be arranged on a covering apparatus assigned to the receiving volume. In particular, it is possible for the plasma source to be integrated in the covering apparatus. This covering apparatus is preferably configured in order to cover the receiving volume such that a closed volume is formed. It is in particular possible for the covering apparatus to be designed as a cover.

The covering apparatus preferably has a heating apparatus by means of which the covering apparatus can be heated at least regionally, in particular at a relevant surface facing the cleaning fluid while the device is operating in order to prevent undesirable condensation on the covering apparatus. The heating apparatus is preferably designed as an electrical heating device, in particular as a heating wire or heating winding, as an infrared heater, as a thermoelectric element, in particular as a Peltier or Seebeck element, or in another suitable manner. The plasma source and the heating apparatus can be provided together and preferably integrally with each other on the covering apparatus. It is possible to use a part, in particular an electrode, of the plasma source as a heating element, in particular as a heating wire for the heating apparatus.

With such a simple embodiment of the device, it is possible to mix the cleaning fluid with the plasma product by shaking, wherein in particular after the plasma is generated by the plasma source, the receiving volume is shaken with a mounted covering apparatus so that the plasma-containing air space and the cleaning fluid are mixed in the receiving volume. It is possible in this case to use the covering apparatus, in particular the cover that has the plasma source for shaking. It is however also possible for the device to also have second covering apparatus, in particular a second cover in addition to a first covering apparatus that has a plasma source, wherein the second covering apparatus is free from a plasma source. This can be used for shaking. In this case, the plasma is preferably first generated with the first covering apparatus; then the first covering apparatus is removed from the receiving volume, and the second covering apparatus is placed on the receiving volume, and the covered volume is then shaken.

According to a development of the invention, the receiving volume is formed or arranged in a receiving container. It is also possible for the receiving volume to be designed as a receiving container. Particularly preferably, it is a cup-shaped receiving container, in particular a cup. It can for example have the size and/or shape of a toothbrush cup or a cleaning glass for dental prosthetics. The receiving volume can thus be provided very easily and conveniently. Preferably, the receiving container can be removed from the device, or from other parts of the device. The receiving container is preferably part of the device.

According to a development of the invention, the plasma source is arranged separately from the receiving volume. This means in particular that the plasma source is arranged spatially separate from the receiving volume, in particular outside of the receiving container that has the receiving volume. Is it is also possible for the plasma source to be arranged and configured in order to generate a plasma in air that originates from the air space above the cleaning fluid. It is however also possible for the plasma source to be arranged and configured to generate a plasma in another medium, in particular in another gaseous medium which is then preferably supplied to the cleaning fluid in the receiving volume.

According to a development of the invention, the plasma source is arranged in a medium line for conducting a gaseous medium. In this case, the plasma source is preferably arranged separately from the receiving volume. The plasma source is configured to generate a plasma in the gaseous medium conducted by the medium line. The plasma is preferably generated outside of the receiving volume, and in particular outside of the receiving container. The medium line preferably has a media outlet that terminates in the receiving volume for the cleaning fluid. In this case, the media outlet is preferably arranged such that it terminates in the cleaning fluid below the relevant fill level for the cleaning fluid so that it is therefore provided submersed with regard to the cleaning fluid. The gaseous medium that has the plasma or plasma product can thus be efficiently introduced into the cleaning fluid.

According to a development of the invention, the medium line has a media inlet which terminates in the air space above the relevant fill level of the cleaning fluid in the receiving volume. In this manner, the gaseous medium, in particular air, can be removed from the air space above the cleaning fluid so that plasma, separate from the receiving volume, is generated in the air originating from the air space, and then the plasma product is supplied via the media outlet to the cleaning fluid.

In this case, the plasma source and the medium line are preferably configured so that the gaseous medium can run in a circuit through the medium line and the plasma source. In particular, gaseous medium is thus removed from the air space above the fill level of the cleaning fluid, conducted through the plasma source, then in a state enriched with the plasma product supplied to the plasma cleaning fluid through which it in particular bubbles in the form of gas bubbles, wherein it then exits the cleaning fluid into the airspace and is resupplied from there via the media inlet to the medium line. Preferably, the entire plasma or the entire reactive and/or active species is not thereby absorbed by the cleaning fluid so that the air space also has active and/or reactive species after a certain operating time which then enters the media inlet and reaches the plasma source. In each passage, the plasma source accordingly reinforces a concentration of active and/or reactive species in the gaseous medium, wherein a reinforcement of the activating effect of the gaseous medium on the cleaning fluid simultaneously occurs. A closed circuit is thus provided with recycling of active and/or reactive species to the plasma source which can very quickly produce an activated cleaning fluid.

The plasma source is preferably arranged in the medium line downstream from the media inlet and upstream from the media outlet with reference to a direction of flow of the gaseous medium in the medium line. Preferably a delivery apparatus, in particular a pump, is arranged in the medium line for delivering the gaseous medium along the medium line. The delivery apparatus in this case is particularly preferably arranged upstream from the plasma source.

It is possible for the media inlet to be arranged in the covering apparatus or integrated in the covering apparatus. This allows it to be brought into contact very easily with the air space above the cleaning fluid.

According to a preferred embodiment, the media outlet terminates in an aerator or ventilator. This can in particular be designed as a porous body, in particular as a porous ceramic body. In this manner, the plasma-activated or plasma-containing gaseous medium can be introduced into the cleaning fluid in a particularly effective manner.

Arranging the plasma source separate from the receiving volume moreover has the advantage that it can be decoupled in particular from the receiving container so that the receiving container can be easily disconnected from the rest of the device in and easy and comfortable manner. The arrangement of the plasma source in a medium is very easily scalable, wherein it can be readily adapted to the desired amount of cleaning fluid to be activated.

According to a development of the invention, the device has a base which has a mounting surface for arranging the receiving container. Accordingly, a defined region is created for arranging the receiving container.

Preferably, a control apparatus and/or an electrical storage device is/are provided for the plasma source in the base. A "control apparatus" is in this case understood in particular to be a device by means of which the plasma source can be controlled, in particular activated and deactivated. An "electrical storage apparatus" is in particular understood to be a device by means of which electrical energy can be saved for operating the plasma source. This can be in particular a capacitor, battery or an accumulator. If the control apparatus and/or the electrical storage device is arranged in the base and the plasma source is simultaneously arranged in a covering apparatus, the covering apparatus and the base are preferably electrically connected to each other. This can for example be realized by at least one electrical line and/or a main body common to the base and the covering apparatus.

It is possible for the base to have an inductive power supply, in particular an inductive charger. In this case, preferably an inductive coil is arranged in the floor of the receiving container, in particular a Qi coil for actively connecting to the inductive power supply in the base.

Alternatively or in addition, the control apparatus and/or the electrical storage apparatus is/are preferably arranged in a covering apparatus assigned to the receiving container. If in this case the plasma source is also arranged in the covering apparatus, a particularly easy and also short contact results between the control apparatus and/or the electrical storage apparatus on the one hand and the plasma source on the other hand.

Alternatively or in addition, the control apparatus and/or the electrical storage apparatus is preferably arranged in a grip, in particular a handle of the receiving container. In this case, the covering apparatus can in particular be easily connected for example to an induction coil arranged in the floor of the receiving container.

That the control apparatus and/or the electrical storage apparatus are provided for the plasma source means in particular that the control apparatus and/or the electrical storage apparatus is/are operatively connected to the plasma source, in particular electrically operatively connected so that the plasma source can be controlled by the control apparatus, and/or so that the plasma source can be supplied with electrical energy by the electrical storage apparatus.

According to a development of the invention, the receiving container is configured to receive at least one dental prosthetic. In particular, the receiving container in this case has dimensions that are suitable for receiving the at least one dental prosthesis, but which preferably do not significantly exceed the dimensions of the at least one dental prosthetic, as is the case with a conventional glass or cup for cleaning dental prosthetics or a toothbrush cup. In particular, the receiving container preferably has a volume corresponding at most to twice the volume of a full-bite prosthetic. This makes the device generally handy, and in particular it can be easily arranged for example in a bathroom.

Alternatively or in addition, the device preferably has an application apparatus for supplying the activated cleaning fluid into the mouth of a user. In this case, cleaning fluid is preferably activatable in the receiving volume, in particular can be mixed with the plasma product, and then can be guided by means of the application device from the receiving volume into the mouth of the user. Particularly preferably, the device is designed as an oral irrigator, wherein it preferably has an oral nozzle to which the activated cleaning fluid from the receiving volume can be supplied and by which the activated cleaning fluid can be introduced into the mouth of the user.

According to a development of the invention, the device has an arrangement region for arranging the receiving container. This can for example be a mounting surface on a base, or another type of arrangement region as well. Preferably, the device has a covering apparatus on a main body of the device such that the receiving container can be covered, preferably is covered, by the covering apparatus when it is arranged in the arrangement region. For example, the receiving container can be shifted under the covering apparatus to be carried by the covering apparatus, whereby it is arranged in the arrangement region.

It is particularly preferable for the covering apparatus to be movable on the main body of the device such that it is moved into a covering position covering the receiving container when the receiving container is arranged in the arrangement region. It is for example possible for the covering apparatus to be pivotably mounted on an axis, wherein a movement apparatus can be provided such that the covering apparatus is automatically moved into the covering position when the receiving container is moved in the arrangement region. Preferably, the covering apparatus is moved into an open position when the receiving container is moved from the arrangement region. This for example corresponds to the functioning of certain coffee machines in which a brewing unit is arranged automatically and/or positively controlled on a coffee pot when the coffee pot is moved into a certain growing region of the coffee machine. It is however alternatively also possible for the covering apparatus to be manually movable into the covering position on the one hand and into the open position on the other hand without being positively controlled by the receiving container.

In a particularly preferred exemplary embodiment, the device has an automatic activation apparatus for the plasma source, wherein this is preferably activated automatically when the receiving container is arranged in the arrangement region. This can in particular be combined with a covering apparatus which can automatically be moved into its covering position when the receiving container is arranged in the arrangement region. If the plasma source is arranged in a medium line for conducting a gaseous medium and the medium line has a delivery apparatus for delivering the gaseous medium along the medium line, this delivery apparatus can additionally or alternatively be activated automatically when the receiving container is arranged in the arrangement region.

According to a development of the invention, the device has a mixing apparatus for mixing the plasma product with the cleaning fluid. In this way, comparatively tedious shaking of the receiving volume can in particular be avoided because instead, the plasma product is mixed with the cleaning fluid by the mixing device.

According to an embodiment of the device, it is possible for the mixing apparatus to have an atomizer. The atomizer is preferably configured to atomize the cleaning fluid, in particular into a region in which the plasma product is present, in particular in an air space above the receiving volume. The atomizer can in particular be designed as a piezo atomizer, as an ultrasonic atomizer, or in any other suitable manner.

In addition or alternatively, it is possible for the mixing device to have an aerator or ventilator. This is understood to be a device that is configured to introduce a plasma-containing gas or plasma containing air into the cleaning fluid. In this case, it can in particular be a porous body that can be arranged in the cleaning fluid, wherein plasma-containing gas or plasma-containing air can be guided through the porous body and can be introduced into the cleaning fluid from a plurality of channels formed in the porous body. In particular, the porous body can be designed as a ceramic body.

In particular, a plasma product generated externally and/or separately from the remaining device can also be supplied to the cleaning fluid via a ventilator or aerator.

In addition or alternatively, the mixing device preferably has a media outlet for a medium having the plasma source, wherein the media outlet preferably terminates in the receiving volume for the cleaning fluid and is in particular provided submersed with reference to a relevant fill level of the cleaning fluid. In this case, it is possible for the media outlet to terminate in an aerator or ventilator.

The mixing apparatus is preferably arranged in the receiving volume, in particular in the receiving container. The receiving container preferably has at least one power and/or media lead-through by means of which it is possible to supply power, in particular electrical power and/or medium, in particular plasma-containing gas or plasma-containing air through a wall, in particular a floor of the receiving container. A connection for the lead-through can for example be integrated in a base of the device that has a mounting surface for the receiving container. It is possible for the device to be configured to remove an air volume, possibly plasma-containing gas or air, above a fill level of the cleaning fluid and to supply it to the mixing apparatus in the receiving volume, in particular below the fill level.

A fluid line designed for this can preferably be arranged in a grip, in particular a handle, of the receiving container. The fluid line can have a delivery apparatus, in particular a membrane pump.

According to a development of the invention, the device has a gas separating apparatus which is configured to separate gas from the air space above the cleaning fluid from the activated cleaning fluid. By means of a gas separating device, it is possible to remove the activated cleaning fluid and in particular to apply it in the mouth of a user without bringing gaseous residue of the plasma product, in particular ozone, close to the respiratory organs of the user. This is particularly advantageous with a device designed as an oral irrigator.

Preferably, the gas separating device is designed such that a removal site for the activated cleaning fluid is arranged below the relevant or predetermined fill level of the cleaning fluid, i.e., submersed.

The gas separating apparatus can be easily designed as a spout or mouth on the receiving container which discharges from the receiving volume below the relevant fill level, and in particular close to the floor of the receiving container. The activated cleaning fluid can then be easily poured out. The covering apparatus can then be held closed for a certain time until the plasma product has attenuated completely or at least enough to exclude a health hazard from inhalation.

It is possible for a ball or ball valve to be arranged in the spout or mouth, in particular at the height of the relevant fill level or above in order to close the receiving volume to the outside when activated cleaning fluid is not being removed. This can in particular prevent plasma-containing air or gas bubbles from escaping the activated cleaning fluid.

The gas separating apparatus can also be designed as a removal site which is arranged submersed and is connected to an oral nozzle via a fluid line. A check valve can be arranged in such a fluid line, in particular a ball or spherical valve.

The object is also achieved by creating a method for treating, in particular for cleaning objects, in particular dental prosthetics and/or teeth that has the following steps: A nonthermal plasma is generated; a plasma product of the nonthermal plasma is mixed with a cleaning fluid; the cleaning fluid is activated by the plasma product, and the activated cleaning fluid is applied onto an object, in particular onto at least one dental prosthetic and/or at least one tooth. In conjunction with the method, in particular the advantages are realized that were already explained in conjunction with the device. In particular, preferably a device is used in the context of the method according to one of the above-described exemplary embodiments. Analogously, the device is preferably configured to perform embodiments of the method described below.

Preferably in the context of the method, at least one dental prosthetic and/or at least one tooth is disinfected; in particular, a bacterial and/or viral burden on the at least one dental prosthetic and/or the at least one tooth is reduced. Alternatively or in addition, it is possible for the at least one dental prosthetic and/or the at least one tooth to be whitened.

The plasma is preferably generated in an air space above a fill level of the cleaning fluid that has the receiving fluid in a receiving volume, or separate from the receiving volume.

Mixing is preferably such that plasma components, in particular reactive species from the plasma, are absorbed by the cleaning fluid and/or react with the cleaning fluid. It is possible for new or additional active species to be generated in the process which ultimately become active in the treatment of at least one dental prosthetic and/or at least one tooth.

The activated cleaning fluid is preferably used in the mouth of the user or outside of the mouth of the user, in particular in the receiving volume, on at least one dental prosthetic and/or at least one tooth.

The mixing can be performed by shaking or atomizing the cleaning fluid, and/or by ventilating or aerating the cleaning fluid with plasma-containing air or a plasma-containing gas.

It is possible for the activation of the cleaning fluid by the plasma product, in particular mixing the plasma product with cleaning fluid, to be performed at the same time as using the cleaning fluid on the object to be treated, in particular the tooth and/or the dental prosthetic. It is also possible to first activate the cleaning fluid, wherein the activated cleaning fluid is used at a later time on the object to be treated. Before and/or during the treatment, the cleaning fluid is preferably stirred or circulated continuously, and/or mixing of plasma-containing air or a plasma-containing gas with the cleaning fluid is continuously performed.

According to a development of the invention, a ratio of an air volume in which the nonthermal plasma is generated to a volume of the cleaning fluid is selected such that the ratio is at least 1:3 to at most 3:1. In addition or alternatively, it is also possible for a ratio of an air mass in which the nonthermal plasma is generated to a mass of the cleaning fluid to be selected such that the ratio is at least 1:3 to at most 3:1. The term "air" in this context generally addresses a carrier gas in which the nonthermal plasma is generated. In this case, the air can be conventional ambient air, however it can also be any other gas, in particular a pure or high purity gas, or a gas mixture. In a particularly simple instance of the method, ambient air is however used to generate the nonthermal plasma. A gas then does not have to be additionally provided. The ratio of volumes and/or masses of air to cleaning fluid specified here ensures highly efficient activation of the cleaning fluid with simultaneously optimum treatment properties of the activated cleaning fluid. It has namely been shown that this ratio is important in particular for the bactericidal and/or virucidal effect of the activated cleaning fluid.

According to a development of the invention, a duty cycle of a plasma source for generating the nonthermal plasma is selected so that active oxygen species or active nitrogen species predominate in the nonthermal plasma and/or the plasma product, in particular with respect to its concentration. In this case, a "duty cycle" addresses an integral overall activation time of the plasma source during a plasma generation event that does not differ from an actual activation time of the plasma source when the plasma source is operated continuously. If the plasma source is however operated intermittently, in particular pulsed, individual activation phases of the plasma source which are separate from each other over time are less than the overall duty cycle during the plasma generation event. The overall duty cycle or integral duty cycle is then in particular the sum of the activation phases of the plasma source, including the inactive phases arranged between these events.

Alternatively or in addition, it is possible to select a performance of the plasma source for generating the nonthermal plasma so that active oxygen species or active nitrogen species predominate in the nonthermal plasma and/or the plasma product. One can hence advantageously adjust whether active oxygen species or reactive nitrogen species predominate in the nonthermal plasma and/or the plasma product by the duty cycle and/or the performance of the plasma source. In particular, the effectiveness of the nonthermal plasma and/or the plasma product, and hence ultimately the activated cleaning fluid as well can thereby be influenced.

"Activated oxygen species" designate in particular molecules, ions, in particular molecular ions, radicals, excited atoms or molecules, or especially reactive molecules that are substantially formed from oxygen and/or substantially have oxygen atoms. An example of such an active oxygen species is ozone.

"Active oxygen species" designate those species that are formed from nitrogen and/or have nitrogen atoms. Examples of active oxygen species are in particular nitrogen oxides.

A consideration of the reaction kinetics of oxygen chemistry on the one hand and nitrogen chemistry on the other hand reveals that rate constants of ozone formation, in particular those of a rate-determining step, are faster than rate constants for forming nitrogen oxides, and in particular faster than a rate constant for forming nitrogen dioxide from nitrogen and oxygen without the participation of ozone as an intermediate product. Ozone is hence formed in particular on a faster timescale than nitrogen oxides without the participation of ozone. However, there also exist reaction mechanisms in which nitrogen oxides are formed with the participation of ozone. These reaction steps of course require the presence of ozone so that the formation of nitrogen oxides by such reaction mechanisms follows ozone formation. In particular, ozone is also broken down by already formed oxygen-impoverished nitrogen oxides, wherein these nitrogen oxides are oxidized into oxygen-richer nitrogen oxides.

Overall, the oxygen chemistry predominates with shorter duty cycles and lower plasma source performance, whereas the nitrogen chemistry predominates with longer duty cycles and higher plasma source performance.

The specific parameters relevant for plasma chemistry with regard to the duty cycle and/or the performance of the plasma source must be determined by calculations and/or experiments for a specific configuration of the device, and in particular the plasma source as well. This is however readily feasible. For example, an ozone generation rate for a surface microdischarge plasma source in air under normal atmospheric conditions lies within a range of 50 ppm/cm s to 200 ppm/cm s. The treatment time can then be calculated from this in order to provide a specific plasma chemistry.

It has been revealed that active nitrogen species are in particular relevant for a positive long-term effect of the activated cleaning fluid as a bactericide. Contrastingly in consideration of the drinking water quality of the cleaning fluid, predominance of active oxygen species is more suitable.

According to a development of the invention, water is used as the cleaning fluid. In this case, it is in particular easy to configure the treatment of at least one dental prosthetic and/or at least one tooth since water is typically readily available. Particularly preferably, drinking water, and most preferably tap water, is used which is typically available easily and cheaply, as well as in a sufficient amount. Furthermore, tap water typically also has the quality of drinking water. The advantage of the proposed device and method proposed here is that the activated cleaning fluid as well preferably has the quality of drinking water so that this property of the water used as the cleaning fluid is not lost by being activated with the plasma product. The activated cleaning fluid can accordingly be readily introduced into the mouth of a patient and also swallowed without fear of health concerns therefrom.

It is alternatively possible to use an alcoholic solution as the cleaning fluid. An alcoholic solution is in particular understood to be a solution that has at least one alcohol, in particular ethanol or another alcohol as the solvent and/or as the solute. In particular, a solution of at least one alcohol in water, also an aqueous alcoholic solution, or solution of water in at least one alcohol can be used as the alcoholic solution. The alcohol comprised by the solution can additionally contribute to treating the at least one dental prosthetic and/or the at least one tooth. It is also possible for the plasma product to form additional active species in combination with the at least one alcohol, in particular by reacting with the alcohol.

It is alternatively possible to use oxygen-enriched water as the cleaning fluid. In this case, in particular the oxygen chemistry can be enhanced while activating the cleaning fluid so that more active oxygen species, in particular ozone as well as hydrogen peroxide, are formed. In order to enrich the water with oxygen, oxygen tablets can be used, for example. Such oxygen tablets typically have effervescent properties which allow them to also accelerate the absorption of effective species of the nonthermal plasma in water in that they namely contribute to the formation of fine water droplets. Moreover, such oxygen tablets could also influence the air chemistry in the air space in which the nonthermal plasma is formed so that the type and number of arising active species is changed in this case.

It is also possible to use a phosphate-buffered saline solution as the cleaning fluid. Such a solution allows working with a constant pH. By means of different salts, the solution possesses the osmotic pressure of the human organism and is accordingly an isotonic saline solution. Such a solution preferably contains 137 mM sodium chloride, 2.7 mM potassium chloride, and 12 mM overall phosphate, in particular in the form of HPO4' and $H_2PO_4^{2-}$. The pH of such a phosphate-buffered saline solution is preferably 7.4. A liter of such a solution preferably contains 8.0 g sodium chloride, 0.2 g potassium chloride, 1.42 g disodium hydroxide phosphate or 1.78 g disodium hydrogen phosphate dihydrate, and 0.27 g potassium dihydrogen phosphate. A phosphate-buffered isotonic saline solution is particularly physiologically harmless.

According to a development of the invention, an activated cleaning fluid is generated that has a hydrogen peroxide content less than that of the threshold for nonprofessional dental whiteners (currently 0.1%) applicable in the European Union on the date determining the priority of the present application. The amount of hydrogen peroxide is particularly preferably less than 0.1%, preferably at this juncture and in the following indicated in % by volume. Conventional whiteners that are used for professionally whitening dental prosthetics and/or teeth have much higher hydrogen peroxide contents (up to 6%) which can in particular be approximately 10 times higher than the legally set threshold for nonprofessional teeth whiteners (presently 0.1%). It was revealed that the activated cleaning fluid according to the invention proposed here and the method proposed here can have an equivalent whitening effect due to additional active and in particular whitening species as with a hydrogen peroxide content of 1%, and nonetheless can have a much lower hydrogen peroxide content, in particular less than 0.1%.

Alternatively or in addition, an activated cleaning fluid is preferably generated that has the quality of drinking water.

"Quality of drinking water" is understood to mean that the activated cleaning fluid can be drunk by humans like drinking water without negative health effects. Preferably, "quality of drinking water" is understood to mean a correspondence between the activated cleaning fluid and legal drinking water standards, in particular the legal drinking water standard of the European Union on the date establishing the priority of the present application. Given the plurality of different reactive species in the activated cleaning fluid that cause interactions in complicated processes for an efficient treatment of dental prosthetics and/or teeth, individual concentrations of the species can be low enough for the activated cleaning fluid to have the quality of drinking water.

The description of the device on the one hand and the method on the other hand are to be understood as being complementary to each other. Features of the device that were described explicitly or implicitly in conjunction with the method are preferably individual or jointly-combined features of a preferred exemplary embodiment of the device. Method steps that were described explicitly or implicitly in conjunction with the device are preferably individual or jointly-combined steps of a preferred exemplary embodiment of the device. The method is preferably distinguished by at least one step that is characterized by at least one feature of an exemplary embodiment of the device which is according to the invention or preferred. The device is preferably distinguished by at least one step that is characterized by at least one step of an embodiment of the method which is according to the invention or preferred.

BRIEF DESCRIPTION OF THE DRAWINGS

In the following, the invention is explained in more detail with reference to the drawing. In the following.

DETAILED DESCRIPTION

Figure 1:
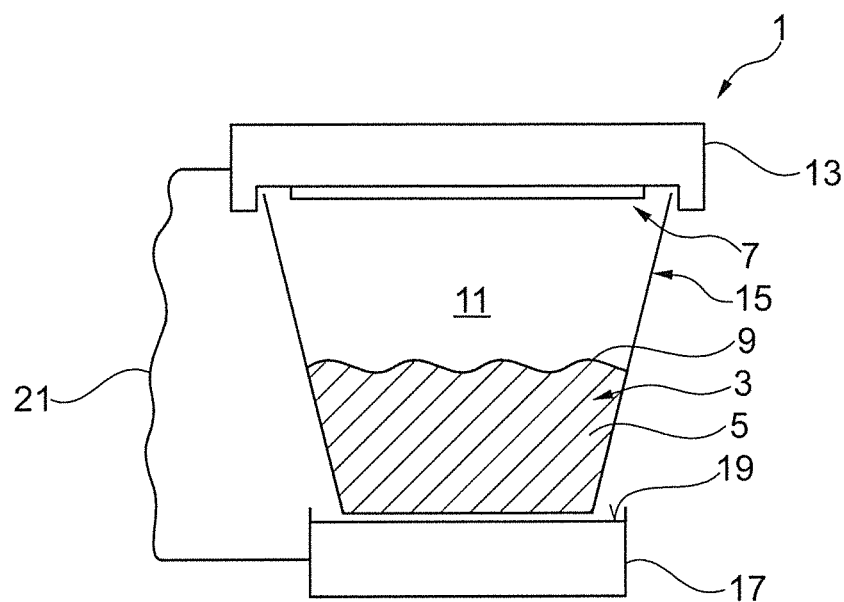
FIG. 1 shows a schematic representation of a first exemplary embodiment of a device for treating objects, in particular dental prosthetics and/or teeth.

FIG. 1 shows a schematic representation of a first exemplary embodiment of a device 1 for treating, in particular for cleaning, most particularly for disinfecting and/or whitening objects, in particular dental prosthetics and/or teeth. The device has a receiving volume 3 which is configured to receive cleaning fluid 5, wherein preferably water, in particular drinking or tap water, an alcoholic solution, water enriched with hydrogen, and/or a phosphate-buffered saline solution is used as the cleaning fluid 5.

The device 1 has a plasma source 7 which is configured to generate a nonthermal plasma. The plasma source 7 is arranged in the exemplary embodiment portrayed here such that it can act on an air space 11 arranged in the receiving volume 3 above the fill level 9 of the cleaning fluid 5 which for example can be predetermined by a fill level marking. The plasma source 7 is integrated here on a covering apparatus 13 assigned to the receiving volume 3, in particular in the covering apparatus 13. The covering apparatus 13 is designed here as a cover for an in particular cup-like receiving container 15, wherein the receiving volume 3 is arranged in the receiving container 15. By means of the covering apparatus 13, the receiving container 15 can be covered, whereby the receiving volume 3 is provided as a closed volume.

The exemplary embodiment of the device 1 shown here has a base 17 that has a mounting surface 19 for arranging the receiving container 15. In this case in the exemplary embodiment shown here, a control unit apparatus (not shown) and/or an electrical storage apparatus (also not shown) for controlling and/or supplying the plasma source 7 is arranged in the base 17. The covering apparatus 13 and in particular the plasma source 7 arranged therein or thereupon is/are connected here by an electrical connecting line 21 to the base 17.

It is alternatively however also possible for the control apparatus and/or the electrical storage apparatus, in particular together with the plasma source 7, to be arranged in the covering apparatus 13. In this case, it is also possible to dispense with the base 17.

In the context of a preferred embodiment of the method for treating dental prosthetics and/or teeth, the cleaning fluid 5 is preferably arranged in the receiving container 15. The receiving container 15 is then closed with the assistance of the covering apparatus 13, and the nonthermal plasma is generated in the air space 11 by means of a plasma source 7.

The device 1 is configured to mix a plasma product, in particular of the nonthermal plasma, with the cleaning fluid 5 in order to generate an activated cleaning fluid. Such mixing can in particular be carried out by shaking the receiving container 15 in the exemplary embodiment portrayed in FIG. 1 so that the active substances from the plasma are as it were shaken out of the plasma into the cleaning fluid 5, or absorbed into it so that the cleaning fluid is activated. Shaking preferably occurs when the receiving container 15 is in a covered state, wherein it is possible to use the covering apparatus 13 for covering. It is however also possible for a separate cover or separate, second covering apparatus to be provided without a plasma source so that, after the plasma is generated, the first covering apparatus 13 is removed, and the separate, second covering apparatus is placed on the receiving container 15. The receiving vessel 15 can then be shaken to activate cleaning fluid.

The device 1 is moreover configured for using the activated cleaning fluid on at least one dental prosthetic and/or at least one tooth. With the device 1 portrayed here, it is easily possible in this case to arrange a digital prosthetic in the receiving container 15, in particular to insert it in the activated cleaning fluid so that it is preferably completely covered by the activated cleaning fluid. The dental prosthetic can then rest for a predetermined time in the receiving container 15 and thereby be cleaned, in particular disinfected, and/or whitened.

The receiving container 15 is preferably designed like a toothbrush cup or toothbrush glass.

It is also possible for the activated cleaning fluid to be used in the mouth of the user, for example by rinsing or gargling. Since the activated cleaning fluid preferably has the quality of drinking water, it is harmless when it is at least partially swallowed by the user.

Figure 2:
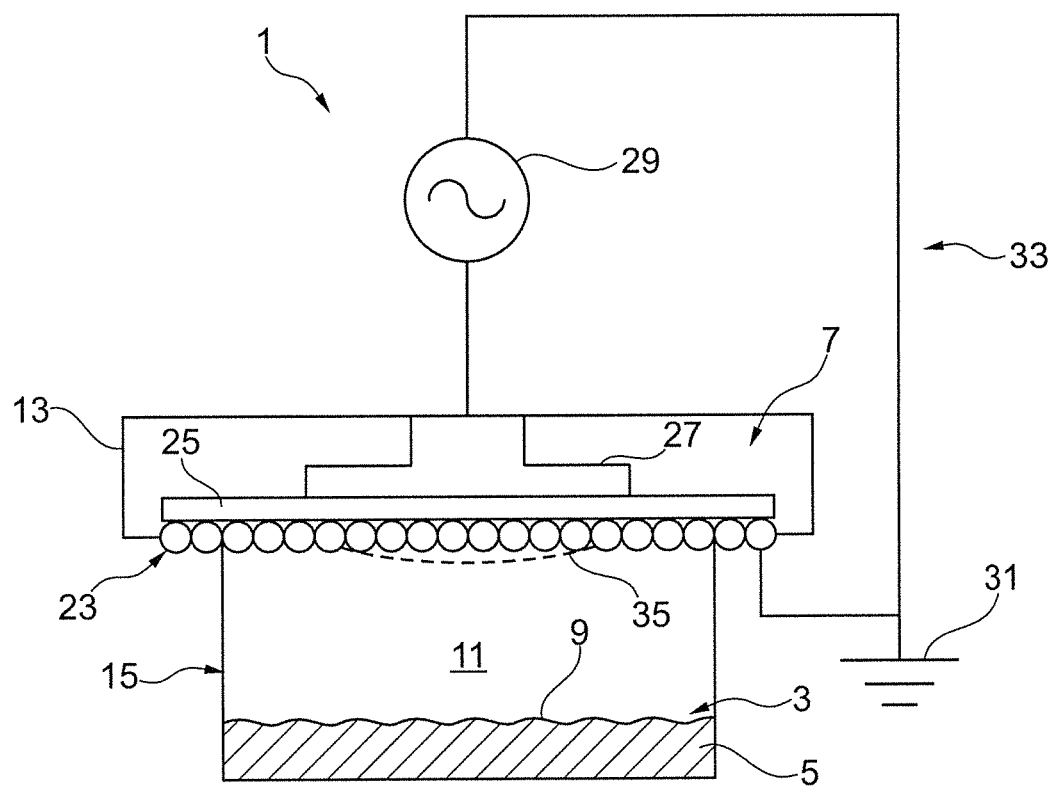
FIG. 2 shows a schematic detailed representation of an exemplary embodiment according to FIG. 1.

FIG. 2 shows a detailed representation of the device 1 according to FIG. 1, wherein in particular the plasma source 7 is further clarified. The same and functionally equivalent elements are provided with the same reference signs so that reference is made to the preceding description. The plasma source 7 functions in this case according to the principle of dielectric barrier discharge (DBD). In this case, a first electrode 23 is spaced by a dielectric 25 that for example can be designed as a glass plate from the second electrode 27, wherein the electrodes 23, 27 are each arranged here on opposite surfaces of the dielectric 25. In this case, the first electrode 23 is arranged on a side of the dielectric 25 facing the air space 11, wherein the second electrode 27 is arranged on a side of the dielectric 25 facing away from the air space 11. The first electrode 23 can also be embedded in the dielectric 25.

The first electrode 23 is preferably designed as a grid electrode that can in particular be formed from individual conductor elements which are arranged distributed in the shape of a grid over the surface of the dielectric 25.

The second electrode 27 is connected to an electrical power source 29, in particular a voltage source, in particular such that a potential different from ground can be applied to the second electrode 27. The power source 29 can in particular be configured as an alternating voltage source so that an alternating voltage can be applied to the second electrode 27.

The first electrode 23 is preferably connected to a ground connection 31. It can be a ground connection 31 of the power source 29, or a ground connection 31 that is however external therefrom.

Reverse contacting the electrodes 23, 27 is also possible, wherein however the first electrode 23 facing a user is preferably applied to ground for reasons of safety.

The power source 29 is preferably part of a control apparatus 33 for controlling the plasma source 7. If the power source 29 is activated and a voltage, in particular an alternating voltage, is accordingly applied to the second electrode 27, a nonthermal plasma 35 (schematically indicated in this case) is generated in the air space 11.

It is possible for both electrodes 23, 27 to be embedded in the dielectric 25 and hence in particular to be encapsulated. The electrode arrangement of the plasma source can be designed very thin, wherein in particular it can have a thickness or strength of at least 20 µm up to at most 500 µm, preferably up to at most 300 µm. The electrode arrangement is accordingly very flexible and can be readily brought into a shape that is useful for the device 1.

Figure 3:
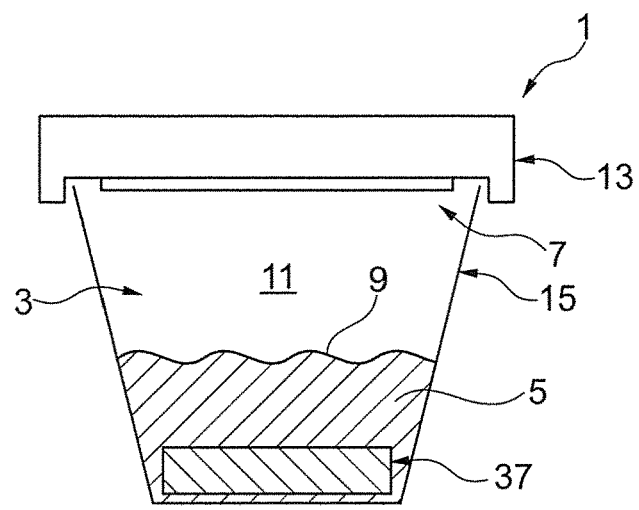
FIG. 3 shows a schematic representation of a second exemplary embodiment of the device.

FIG. 3 shows a schematic representation of a second exemplary embodiment of the device 1. The same and functionally equivalent elements are provided with the same reference signs so that reference is made to the preceding description. The exemplary embodiment portrayed here does not have a base 17. In this case, the control apparatus 33 and preferably the electrical storage apparatus for the plasma source 7 are preferably integrated in the covering apparatus 13. It is however also possible for this exemplary embodiment which is further explained in the following to have a base 17 and accordingly be designed like the exemplary embodiment portrayed in FIG. 1. It is also possible for the plasma source 7 in the exemplary embodiment according to FIG. 3 to be designed as portrayed in FIG. 2.

In the exemplary embodiment portrayed in FIG. 3, a mixing apparatus 37 is provided which is only schematically portrayed in this case. The mixing apparatus 37 can be designed as an atomizer, in particular as a piezo or ultrasonic atomizer, or also as a ventilation apparatus, in particular as an aerator. If the mixing apparatus 37 is designed as an aerator, it preferably has a porous ceramic through which plasma-containing air from the air space 11 can be introduced into the cleaning fluid 5. For this, preferably a fluid line is provided to the air space 11 that is not shown in FIG. 3. If the mixing device 37 is provided, bothersome shaking of the receiving container 15 or other parts of the device 1 is unnecessary. Instead, the mixing can be easy, comfortable and reproducible by means of the mixing device 37.

Figure 4:
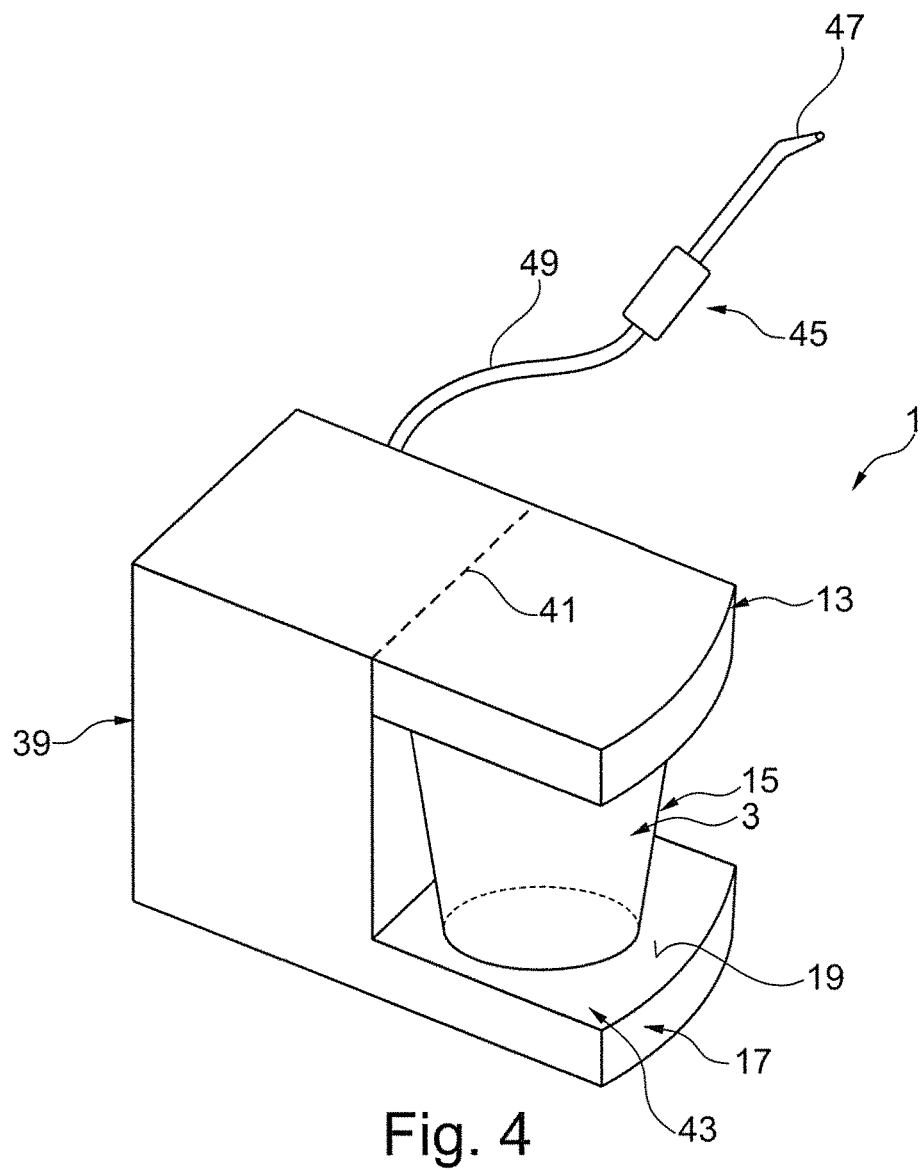
FIG. 4 shows a schematic representation of a third exemplary embodiment of the device.

FIG. 4 shows a schematic representation of a third exemplary embodiment of the device 1. The same and functionally equivalent elements are provided with the same reference signs so that reference is made to the preceding description. In the present exemplary embodiment, the covering apparatus 13 and the base 17 are arranged on a common main body 39 of the device 1, wherein the control apparatus and/or the electrical storage apparatus for the plasma source 7 can be arranged in the main body 39 or integrated therein. Moreover, an apparatus which may be provided for operating the mixing apparatus 37 (not explicitly shown here) can be arranged in the main body 39 or integrated therein, for example a control apparatus for operating a piezo atomizer, or a pump for delivering plasma-containing gas or air to an aerator. The base 17 can in particular have a connecting apparatus integrated in the mounting surface 19 to which a leadthrough through a wall, in particular the floor, of the receiving container 15 can be connected for connecting the mixing apparatus 37 when the receiving container 15 is arranged on the mounting surface 19. The leadthrough can be an electrical leadthrough and/or a fluid leadthrough. Plasma-containing air or plasma-containing gas can also be removed from the air space 11 via the covering apparatus 13 which then preferably has a corresponding suction opening as well as a corresponding fluid line.

In the exemplary embodiment of the device 1 portrayed here, the covering apparatus 13 is movably arranged on the main body 39, namely pivotable here in particular about a hinge axis 41. The covering apparatus 13 is therefore pivotable upward into an open position and downward into a covering position, wherein it covers the covering container 15 in the covering position. It is alternatively also possible for the covering device 13 to be pivotable into an open position about an oblique axis, in particular perpendicular to the hinge axis 41 to the side of the covering position portrayed in FIG. 4. It is also possible that the covering apparatus 13 can be provided on the main body 39 so as to be otherwise movable, in particular linearly movable as well, for example upward in order to be movable into an open position on the one hand and into a covering position on the other hand. The covering apparatus 13 is preferably arranged so as to be movable on the main body 39 so that it can be moved into the covering position when the receiving container 15 is arranged in an arrangement region 43 provided therefor. In this case, the covering apparatus 13 can in particular be automatically closed, wherein it is preferably also automatically openable, i.e., can be moved into its open position, when the receiving container 15 is removed from the arrangement region 43.

Particularly preferably, the plasma source 7 can be automatically activated when the covering apparatus 13 is closed, and in particular when the receiving container 15 is arranged in the arrangement region 43.

Figure 5:
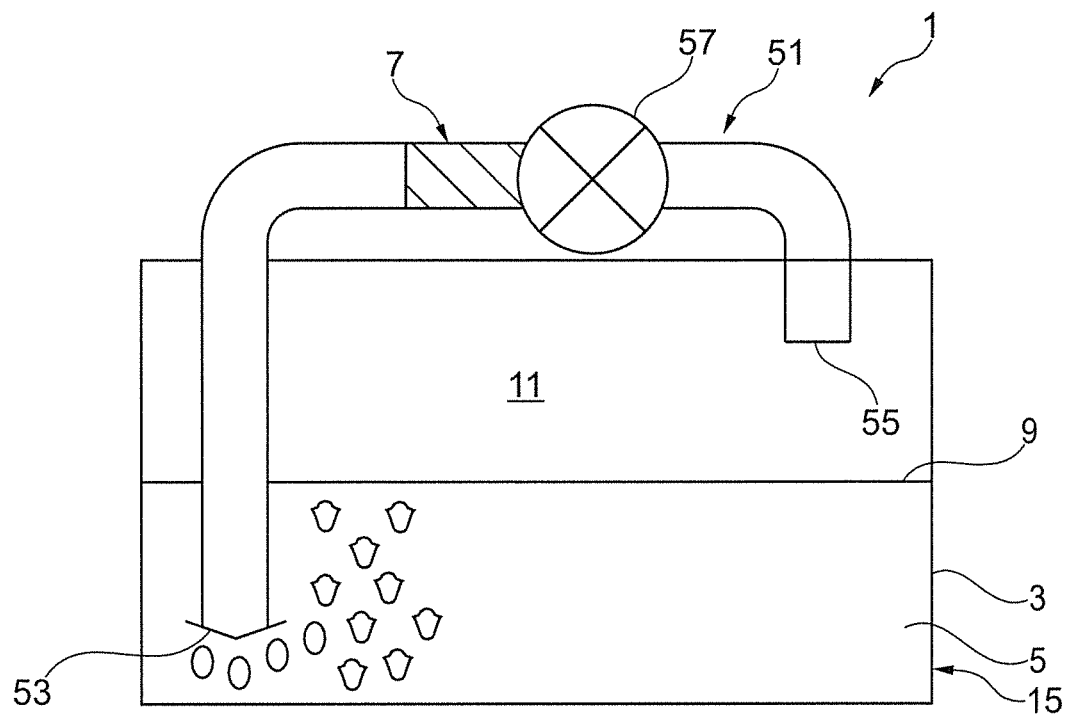
FIG. 5 shows a schematic representation of a fourth exemplary embodiment of the device.

FIG. 5 shows a schematic representation of a fourth exemplary embodiment of the device 1. The same and functionally equivalent elements are provided with the same reference signs so that reference is made to the preceding description. With the exemplary embodiment portrayed here, the plasma source 7 is arranged separately from the receiving volume 3, wherein it is in particular arranged outside of the receiving container 15. The plasma source 7 is in particular arranged in a medium line 51, wherein the medium line 51 is designed to convey a gaseous medium. The plasma source 7 is arranged and configured such that a plasma can be generated by the plasma source 7 in the gaseous medium conveyed by the medium line 51. The medium line 51 has a media outlet 53 that terminates in the receiving volume 3 below the fill level 9, i.e., submersed in the cleaning fluid 5. In this case, it is in particular possible for the media outlet 53 to terminate in an aerator or ventilator.

The medium line 51 has a media inlet 55 that terminates in the air space 11 above the relevant fill level 9 for the cleaning fluid 5. A delivery apparatus 57 is arranged in the medium line 51 that serves to deliver the gaseous medium along the medium line 51 from the media inlet 55 via the plasma source 7 to the media outlet 53. The plasma source 7 in this case is arranged in the medium line 51 downstream from the media inlet 55 and upstream from the media outlet 53. The delivery apparatus 57 is arranged upstream from the plasma source 7 in the exemplary embodiment portrayed here.

The plasma source 7 can have a hollow electrode arrangement, in particular a cylindrical electrode arrangement or also one that has a polygonal cross-section, or also at least one planar electrode arrangement, or a stacked arrangement of planar electrodes. It is also possible for the plasma source 7 to have a perforated electrode arrangement through which the gaseous medium is conducted.

The exemplary embodiment portrayed in FIG. 5 can preferably be combined with the exemplary embodiment portrayed in FIG. 4 such that the plasma source 7 is arranged on or in the main body 39, wherein the medium line 51 preferably extends through the main body 39 or along the main body 39. The delivery apparatus 57 is also preferably arranged on or in the main body 39. The media inlet 55 can preferably be integrated in the covering apparatus 13, or arranged in the covering apparatus 13. The media outlet 53 can in turn preferably be arranged on or in the base 17, in particular in the form of a leadthrough, in particular integrated in the base 17. The medium line 51 can then in particular run from the covering apparatus 13 through the main body 39 into the base 17.

Figure 6:
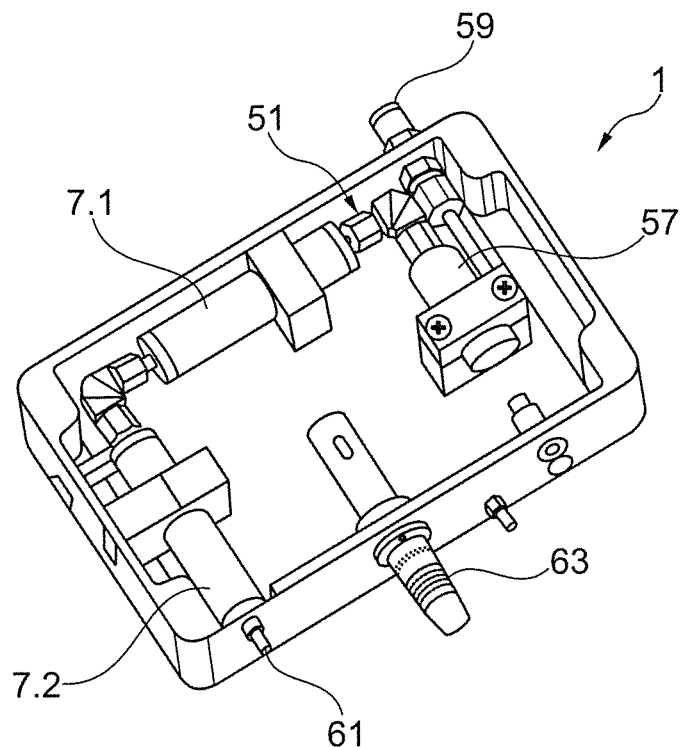
FIG. 6 shows a schematic representation of a fifth exemplary embodiment of the device.

FIG. 6 shows a representation of a fifth exemplary embodiment of the device 1. The same and functionally equivalent elements are provided with the same reference signs so that reference is made to the preceding description. In this case, a unit which in particular can be arranged separately from the receiving volume 3 and in particular separately from the receiving container 15 is portrayed here and has the plasma source 7, the delivery apparatus 57 and in part the medium line 51. This apparatus can be provided as a separate assembly. In this context it has a first line connector 59 which serves to connect to a section of the medium line 51 that runs to the media inlet 55, as well as a second line connector 61 which serves to connect to a section of the medium line 51 which leads to the media outlet 53. In this context, the plasma source 7 has two cylindrical electrode arrangements 7.1, 7.2. An electrical leadthrough 63 is also portrayed by means of which the electrode arrangement 7.1, 7.2 can be contacted.

With the embodiments of the device 1 according to FIGS. 5 and 6, plasma-containing air can be guided via the air space 11, the medium line 51 and the cleaning fluid 5 in a circuit so that an active operating state of the device 1 can be established very quickly.

In all of the exemplary embodiments of the device 1 described up to this point, it is possible to configure the receiving container 15 to receive at least one dental prosthetic. In particular, but not exclusively, it is additionally or alternatively possible in the exemplary embodiment portrayed in FIG. 4 to provide an application apparatus 45 which is configured to supply the active cleaning fluid into the mouth of a user. For this, the application apparatus 45 can in particular have an oral nozzle 47. The device 1 is accordingly preferably formed overall as an oral irrigator. The application apparatus 45 preferably has a hose connection 49 by means of which it is connected in particular to the main body 39. A pump, etc. can be arranged in the main body 39, wherein by means of this pump etc., activated cleaning fluid can be delivered from the receiving volume 3 through the hose connection 49 and the oral nozzle 47 into the mouth of the user. To remove the activated cleaning fluid from the receiving volume 3, a fluid leadthrough in particular in a wall, in particular a floor of the receiving container 15 can be used which can be connected to a corresponding connecting device or docking site in the mounting surface 19.

In a preferred embodiment of the method proposed here, a ratio of an air volume and/or an air mass in which the nonthermal plasma is generated to a volume and/or mass of the cleaning fluid 5 of at least 1:3 to at most 3:1 is selected.

A duty cycle and/or a performance of the plasma source 7 for generating the nonthermal plasma is preferably selected so that active oxygen species or active nitrogen species predominate in the nonthermal plasma.

Preferably, an activated cleaning fluid is generated that has a hydrogen peroxide content below a threshold applicable in the European Union on the priority date of the application for nonprofessional teeth whitening, and/or that has the quality of drinking water.

Figure 7:
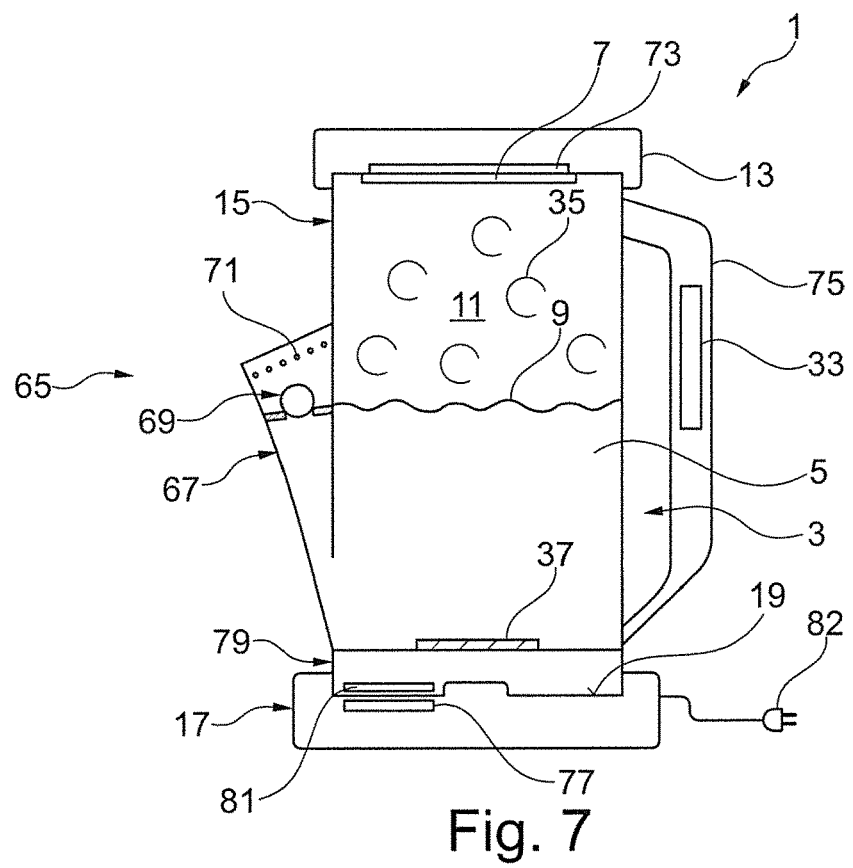
FIG. 7 shows a schematic representation of a sixth exemplary embodiment of the device.

FIG. 7 shows a representation of a sixth exemplary embodiment of the device 1. The same and functionally equivalent elements are provided with the same reference signs so that reference is made to the preceding description. The device 1 in this context has a gas separating apparatus 65 in the form of a nozzle 67 arranged on the receiving container 15 which terminates submersed, i.e., below the fill level 9 in the receiving volume 3. It is accordingly possible to pour out the activated cleaning fluid without simultaneously removing gaseous components, in particular ozone, of the plasma product.

A check valve in the form of a ball valve 69 is integrated in the spout 67. A grating 71 prevents the shut-off ball of the ball valve 69 from falling out and can at the same time optionally be used to filter the cleaning fluid.

The device 1 also has a heating apparatus 73 integrated in the covering apparatus 13 which in particular is provided to prevent undesired condensation.

The receiving container 15 has a handle 75 in which in this context the control apparatus 33, for example, as well as preferably a battery, etc. is/are integrated.

The mixing apparatus 37 is designed in this context as a piezo atomizer.

The base 17 has an inductive voltage supply 77, wherein an induction coil 81 is integrated in a floor 79 of the receiving container. The inductive voltage supply is assigned a mains plug 82 in this context.

Figure 8:
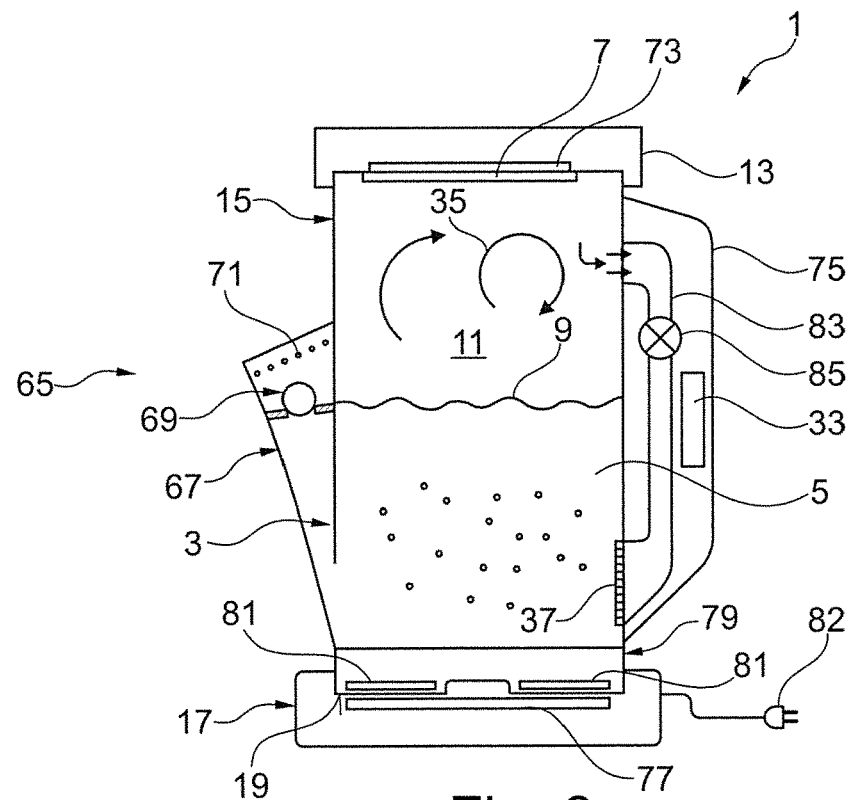
FIG. 8 shows a schematic representation of a seventh exemplary embodiment of the device.

FIG. 8 shows a representation of a seventh exemplary embodiment of the device 1. The same and functionally equivalent elements are provided with the same reference signs so that reference is made to the preceding description. In the following, differences from the sixth exemplary embodiment according to FIG. 7 will be addressed in particular: In the exemplary embodiment portrayed here in FIG. 8, the fluid line 83 is integrated in the handle 75 by means of which the plasma-activated air, as indicated by arrows, can be removed from the air space 11 and supplied to the mixing apparatus 37 designed here as an aerator. For this, a fluid delivery device 85, preferably a membrane pump, is arranged in the fluid line 83.

Figure 9:
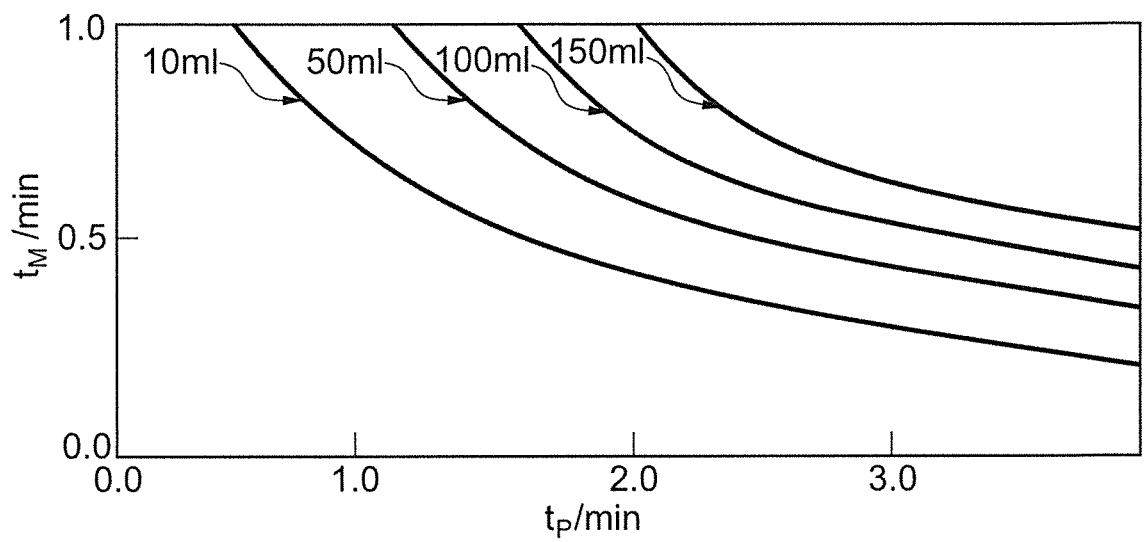
FIG. 9 shows a diagrammatic representation of the relationship between a mixing time, the duty cycle of a plasma source, and the bactericidal effect of a cleaning fluid produced by means of the device according to the invention and a method according to the invention.

FIG. 9 shows a diagrammatic representation of the effectiveness of the method proposed in this context. In this case, a duty cycle $t_P$ for the plasma source 7 is plotted on the horizontal axis. A mixing time $t_M$ is plotted in minutes on the vertical axis as the time for mixing the plasma product with the cleaning fluid. Moreover, different limit curves for different volumes of water as the cleaning fluid are indicated in the diagram, wherein the volumes are assigned to the curves by arrows. Bacteria of the *E. coli* type were suspended in the volumes of water. Then the water was arranged in a receiving container. The plasma source was activated for the indicated duty cycle $t_P$, and the thus-generated plasma product was mixed with water for the mixing time $t_M$. The limit curves portrayed here show a limit for each indicated volume, above and to the right of which a region is indicated in which the bacteria were reduced in the water by more than 6 orders of magnitude. If the respective limit line is exceeded at higher duty cycles of the plasma source, and/or at higher mixing times, the reduction of bacteria in the water by plasma activation is more than 6 orders of magnitude. This can be expressed in particular as a so-called sterility assurance level (SAL), wherein an SAL value can also be used for evaluating a sterilization process. A reduction by 6 orders of magnitude means a reduction of the bacteria burden by a factor of $10^6$, which normally is also termed a 6-log reduction in terms of an SAL value.

With reference to FIG. 9, it is shown that the method proposed here and the device proposed here are extremely efficient, and a significant reduction of a bacteria burden can be achieved within a short time. A similar case cannot be prevented for viruses because a reduction by more than 8 orders of magnitude was revealed in each experiment, so that nearly all of the viruses were deactivated within the measured times.

Figure 10:
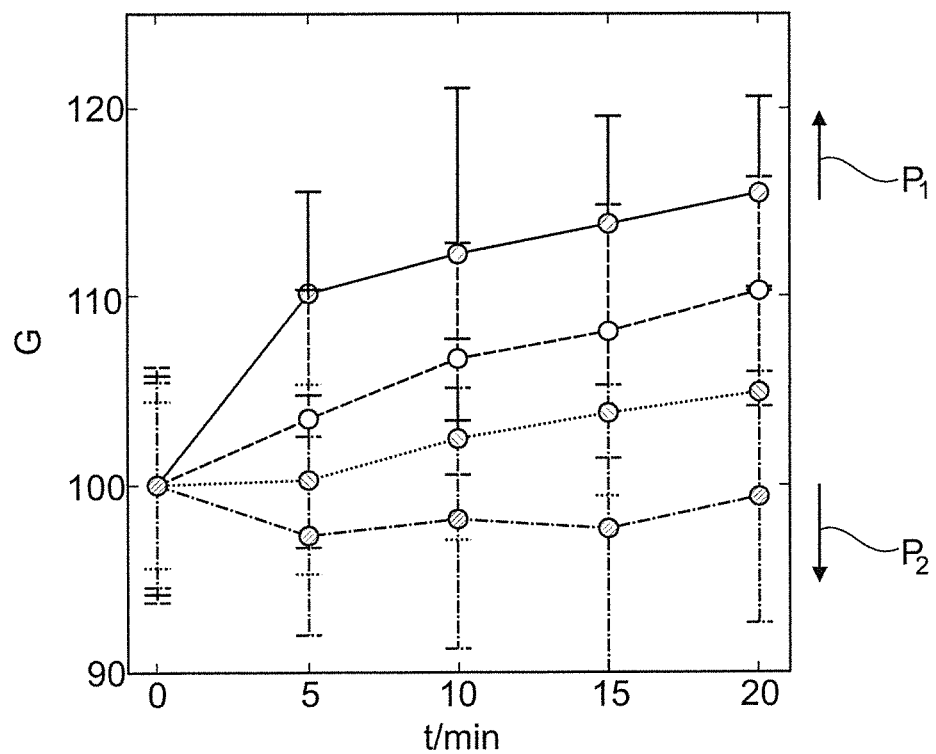
FIG. 10 shows a diagrammatic representation of the efficiency of an embodiment of the method according to the invention for whitening objects, in particular for whitening teeth.

FIG. 10 shows a diagrammatic representation of the effectiveness of an embodiment of the method according to the invention for whitening objects, in particular teeth and/or dental prosthetics. In this case, a standardized gray value G in minutes of an object, in particular a dental prosthetic or a tooth is plotted here against a treatment time t. A first arrow $P_1$ points in the direction of brighter, standardized gray values. A second arrow $P_2$ points in the direction of darker, standardized gray values. A first top, solid curve shows the results of a whitening treatment with the method according to the invention using an activated cleaning fluid based on water with a hydrogen peroxide content of less than 0.1%. A second dashed curve portrayed below the first curve shows the results of a whitening treatment with a 1% aqueous hydrogen peroxide solution. A third dotted curve arranged below the second curve shows the results of a treatment with non-activated water not containing hydrogen peroxide. A fourth dot-dashed curve portrayed below the third curve shows control values that were taken without any treatment. The error bar drawn in each case shows the bandwidth of the variation in the different experiments. It is clearly revealed that treatment with plasma-activated water as portrayed in the first solid curve provides a significantly better whitening effect over the same length of treatment than treatment with aqueous 1% hydrogen peroxide solution according to the second dashed curve.

Overall, it is revealed that an option is created with the method proposed here, and the device 1 proposed here which is as simple as it is efficient, and simultaneously harmless with regard to the health the user, in particular for treating dental prosthetics and/or teeth.

The invention claimed is:

1. A device for treating objects, comprising:
    a receiving volume arranged in a receiving container for receiving a cleaning fluid; and
    a plasma source configured to generate a nonthermal plasma,
    wherein the device is configured to mix a plasma product with cleaning fluid via a mixing apparatus, whereby an activated cleaning fluid can be generated,
    wherein the device is configured to take gas from an air space above a fill level of the cleaning fluid and to supply the gas via a conduit to the mixing apparatus arranged in the receiving volume below the fill level,
    wherein the plasma source is arranged and configured for generating the nonthermal plasma in the gas conveyed in the conduit,
    wherein the conduit is configured as a medium line having a media inlet which terminates in the air space above the fill level of the cleaning fluid in the receiving volume and a media outlet which terminates at the mixing apparatus, and
    wherein the device is configured to use the activated cleaning fluid on an object.

2. The device according to claim 1, wherein the plasma source is arranged in the conduit.

3. The device according to claim 1, wherein the device has a base which has a mounting surface for arranging the receiving container, and wherein a control apparatus and/or an electrical storage apparatus for the plasma source is arranged:
    in the base and/or
    in a covering apparatus assigned to the receiving volume.

4. The device according to claim 1, wherein:
    the receiving container is configured to receive at least one dental prosthesis, and/or
    the device has an application apparatus for supplying the activated cleaning fluid into the mouth of a user.

5. The device according to claim 1, wherein the device has an arrangement region for arranging the receiving container, and wherein a covering apparatus can be moved on a main body of the device so that the covering apparatus is moved into a covering position covering the receiving container when the covering container is arranged in the arrangement region.

6. The device according to claim 1, wherein the mixing apparatus has:
    an atomizer, a ventilating apparatus, and/or the media outlet of the medium line having the plasma source.

7. The device according to claim 1, wherein the conduit has the media inlet arranged above the fill level of the cleaning fluid.

8. The device according to claim 1, wherein the conduit has an outlet below the fill level of the cleaning fluid.

9. The device according to claim 8, wherein the mixing apparatus is the outlet of the conduit.

10. The device according to claim 1, wherein the conduit has a conveying apparatus.

11. A method for treating the objects, comprising using the device of claim 1:

to generate the non-thermal plasma;
to mix the plasma product with the cleaning fluid;
to activate the cleaning fluid with the plasma product, and
to use the activated cleaning fluid on the object.

12. The method according to claim 11, wherein a ratio of an air volume in which the nonthermal plasma is generated to a volume of the cleaning fluid is selected to be at least 1:3 to at most 3:1.

13. The method according to claim 11, wherein a duty cycle and or a performance of the plasma source for generating the nonthermal plasma is selected so that:

active oxygen species or
active nitrogen species
predominate in the plasma product.

14. The method according to claim 11, wherein:

water;
an alcoholic solution;
oxygen-enriched water, and/or
a phosphate-buffered saline solution is used as the cleaning fluid.

15. The method according to claim 11, wherein the activated cleaning fluid is generated that has:

a hydrogen peroxide content less than that of a threshold for nonprofessional dental whiteners applicable in the European Union on the date determining the priority of the present application, and/or
the quality of drinking water.

* * * * *